United States Patent [19]

Hughes et al.

[11] Patent Number: 4,614,793
[45] Date of Patent: Sep. 30, 1986

[54] HEPATITIS A—SUBUNIT ANTIGEN

[75] Inventors: Joseph V. Hughes, Harleysville; Edward M. Scolnick, Wynnewood; Joanne E. Tomassini, Harleysville, all of Pa.

[73] Assignee: Merck & Co., Inc., Rahway, N.J.

[21] Appl. No.: 585,942

[22] Filed: Mar. 2, 1984

Related U.S. Application Data

[63] Continuation-in-part of Ser. No. 541,836, Oct. 14, 1983.

[51] Int. Cl.$^4$ ............................................. C07K 15/04
[52] U.S. Cl. .................................. 530/350; 530/418; 530/806; 530/826
[58] Field of Search ......................................... 436/531

[56] References Cited

U.S. PATENT DOCUMENTS 4,382,076  5/1983  Hurni et al. ........................ 436/531

OTHER PUBLICATIONS

Journal of Virology (1984), 465–473, vol. 52, No. 2.
Tratschin et al., Journal of Virology, 38:151–156 (1981).
Coulepsis et al., Intervirology, 18:107–127 (1982).

Primary Examiner—Delbert R. Phillips
Attorney, Agent, or Firm—Donald J. Perrella; Hesna J. Pfeiffer

[57] ABSTRACT

A surface structural protein of Hepatitis A Virus (HAV) has been isolated and characterized from virus grown in tissue culture. This 33,000 dalton viral protein (VP-1) reacts with immune HAV sera and monoclonal antibodies that neutralize HAV infectivity. The VP-1 is usable for the preparation of a polypeptide subunit vaccine for HAV.

Hybridoma cells were made which produced monoclonal antibodies to HAV or VP-1. These monoclonal antibodies were found to neutralize the infectivity of HAV and to compete with polyclonal antibody derived from human HAV immune sera. The monoclonal antibodies are useful for the neutralization of infectious HAV, the detection of antibodies to neutralizing sites on HAV, and the diagnoses of HAV disease in humans and other susceptible hosts.

6 Claims, No Drawings

HEPATITIS A—SUBUNIT ANTIGEN

RELATED CASES

This case is a continuation-in-part of U.S. Ser. No. 541,836, filed Oct. 14, 1983, now pending.

BACKGROUND OF THE INVENTION

Hepatitis A is a liver disease which, although not commonly fatal, can induce long periods of delibitating illness. The disease is commonly spread by direct contact with an infected individual or by hepatitis A virus (HAV) contaminated drinking water and/or food.

The prior art does not identify the protein or proteins of HAV (hepatitis A virus) which induce neutralizing antibodies to this virus. One of the major drawbacks to examining the protective antigenicity of HAV proteins has been the lack of sufficient quantities of HAV and its polypeptide components. The virus is made in very small quantities in cell culture, has a limited animal host range, and is difficult to purify from infected cell cultures and animal tissues.

To make a subunit vaccine to HAV, it is necessary to identify either whole viral proteins or polypeptides that can induce and/or bind to protective or neutralizing viral antibodies.

The existence of four distinct polypeptides in HAV has been reported in studies using electrophoresis of disrupted radioiodinated HAV, Tratschin et al., J. Virol. 38:151-156 (1981); Coulepis et al., Intervirology 18: 107-127 (1982).

OBJECTS OF THE PRESENT INVENTION

It is, accordingly, an object of the present invention to identify a structural protein of HAV hereafter referred to as VP-1 which acts as a major viral antigen which binds to neutralizing antibodies(s) to HAV. Another object of the invention is to provide a method for the isolation of this structural protein. A further object is to provide a method for the use of this structural protein to immunize a susceptible host against HAV. Yet another object is to provide a hybridoma cell which produces monoclonal antibodies which neutralize HAV infectivity. Still another object is to provide a diagnostic reagent incorporating those monoclonal antibodies. These and other objects of the present invention will be apparent from the following description.

SUMMARY OF THE INVENTION

A structural protein (VP-1) of HAV has been isolated. The protein has a molecular weight of 33,000 daltons and is located on the outer surface of the virus. VP-1 is highly reactive with HAV immune sera from several infected hosts including man. The site(s) for binding of monoclonal neutralizing antibodies to HAV are present on VP-1. An amino acid analysis of VP-1 and a partial amino acid sequence of a cyanogen bromide-cleaved peptide of VP-1 have been performed. The VP-1 of HAV is usable in serological testing for HAV antibodies and for the preparation of a polypeptide subunit vaccine for HAV.

Hybridoma cells were selected from a fusion of a myeloma cell line with spleen cells immunized with HAV or VP-1. These hybridoma cells have been cloned to homogeneity and the monoclonal antibodies that are produced neutralize the infectivity of and bind the virus and are directed to VP-1 (see above). Some of the monoclonal antibodies also compete with polyclonal antibodies to HAV derived from sera of HAV infected humans. These monoclonal antibodies can be used in a rapid diagnostic test to measure the presence of antibodies to HAV and can also measure the presence of neutralizing antibodies.

DETAILED DESCRIPTION

HAV is grown in vitro in a susceptible tissue culture system such as, for example, monkey kidney or monkey liver cells. The cells are disrupted, cell debris is removed, for example, by low-speed centrifugation and the virus is isolated from the supernatant liquid. Viral-containing fractions are collected and purified.

The viral infected cells may be disrupted by lysing and sonication in the presence of a nonionic surfactant and a hypotonic buffer. Suitable nonionic surfactants are polyoxyethylated alkyl phenols having from about 4 to about 30 oxyethylene units and an alkyl group of from about 6 to about 15 carbon atoms, a specific example of which is polyoxyethylene(9)octaphenol; polyoxyethylene sorbitan fatty acid esters having from about 4 to about 30 oxyethylene units and a fatty acid of from about 12 to about 20 carbon atoms, some specific examples of which are polyoxyethylene(4)sorbitan monolaurate, polyoxyethylene(4)sorbitan monostearate, polyoxyethylene(5)sorbitan monooleate, polyoxyethylene(20)sorbitan monostearate, polyoxyethylene(20)sorbitan monopalmitate, polyoxyethylene(20)sorbitan monooleate, polyoxyethylene(20)sorbitan trioleate and polyoxyethylene(20)sorbitan tristearate; polyoxyethylene sorbitol esters of fatty acids having from about 12 to about 20 carbon atoms, of mixed fatty acids and resin acids, of lanolin, of beeswax or of tallow esters, some specific examples of which are polyoxyethylene sorbitol oleate, polyoxyethylene sorbitol tall oil, polyoxyethylene sorbitol laurate, polyoxyethylene sorbitol hexa-oleate, and polyoxyethylene sorbitol lanolin derivative; polyoxyethylene acids having from about 8 to about 50 oxyethylene units and a fatty acid of from about 12 to about 20 carbon atoms, some specific examples of which are polyoxyethylene(8)laurate, polyoxyethylene(8)stearate, polyoxyethylene(20)palmitate, polyoxyethylene(40)stearate and polyoxyethylene(50)stearate; and polyoxyethylene alcohols having from about about 2 to about 25 oxyethylene units and an alcohol of from about 12 to about 20 carbon atoms, some specific examples of which are polyoxyethylene(2)cetyl ether, polyoxyethylene(2)oleyl ether, polyoxyethylene(2) stearyl ether, polyoxyethylene(4)lauryl ether, polyoxyethylene(6)tridecyl ether, polyoxyethylene (10)cetyl ether, polyoxyethylene(10)oleyl ether, polyoxyethylene(10)stearyl ether, polyoxyethylene(12) tridecyl ether, polyoxyethylene(12)tridecyl ether urea complex, polyoxyethylene(15)tridecyl ether; polyoxyethylene(20)cetyl ether, polyoxyethylene(20) oleyl ether, polyoxyethylene(20)stearyl ether; and polyoxyethylene(23)lauryl ether; or deoxycholine. Polyoxyethylene(9)octaphenol is a preferred surfactant.

The cell debris from the sonicated cells is removed, e.g., by low-speed centrifugation. The virus may be isolated and purified from the supernatant fluid by various techniques, e.g., centrifugation, column chromatography or immune affinity chromatography.

The purified virus is treated to isolate and resolve major proteins. Isolation may be effected by electroelution from gels, column chromatography or immune affinity chromatography.

Three major HAV proteins are readily resolved by gel electrophoresis following solubilization with an anionic surfactant, preferably in the presence of a reducing agent. The anionic surfactant may be an alkyl sulfate alkali metal salt containing from about 10 to about 20 carbon atoms such as, for example, sodium decyl sulfate, sodium dodecyl sulfate or sodium octadecyl sulfate. The reducing agent may be 2-mercaptoethanol or dithiothreitol. One of the major proteins, a 33,000 dalton protein, VP-1, is much more highly labelled by $I^{125}$ than the other two indicating that it is an outer surface protein. Cyanogen bromide cleavage of VP-1 yields two large polypeptide fragments of about 20,000 and about 14,000 daltons. A repeat cleavage using cyanogen bromide yielded at least four additional smaller fragments.

VP-1 was isolated and analyzed for amino acid concentration after acid hydrolysis. It contained the following amino acids in approximate order of decreasing percent by weight: glycine, serine, glutamic acid and/or glutamine, aspartic acid and/or asparagine, alanine, threonine, leucine, valine, lysine, proline, phenylalanine, arginine, isoleucine, tyrosine, histidine and methionine.

The foregoing amino acids are present in approximately the following percentages by weight:
glycine, from about 21% to about 30%,
serine, from about 9% to about 11%,
glutamic acid and/or glutamine, from about 8% to about 10.5%,
aspartic acid and/or asparagine, from about 7.2% to about 10%
alanine, from about 6% to about 7.3%,
threonine, from about 4.9% to about 8.2%,
leucine, from about 4.9% to about 7.2%,
valine, from about 4% to about 5.4%,
lysine, from about 3.7% to about 4.3%,
proline, from about 3.2% to about 5.3%,
phenylalanine, from about 3% to about 4.5%,
arginine, from about 2% to about 4.1%,
isoleucine, from about 2% to about 3.6%,
tyrosine, from about 2.0% to about 3.0%,
histidine, from about 1.3% to about 1.9%, and
methionine, from about 0.3% to about 0.9%.

Due to the method using gel electrophoresis isolation for the proteins, and the hydrolysis conditions used during analysis, it is noted that the figure given above for glycine is high; that for methionine is low; and no values are observed for cysteine and tryptophan, which are present in the polypeptide.

Cyanogen bromide cleavage of VP-1 yields, as noted previously, at least six fragments. These fragments were found to contain by HPLC analysis the following amino acid sequences from the direction of the amino terminus to the carboxy terminus of the peptide with the amino acid residues shown in parenthesis inferred from the nucleotide sequence:

Sequence
I. Val-Gly-Asp-Asp-Ser-Gly-Gly-Phe-(Ser)-Thr-Thr
II. (Met)-Lys-Asp-Leu-Lys-Gly-Lys-Ala-Asn-Arg-Gly-Lys
III. (Met)-(Asp)-Val-Ser-Gly-Val-Gln-Ala-Pro-Val-Gly-Ala-Ile-Thr-Thr-Ile-Glu-Asp-Pro-Ala-Leu-Ala-Lys-Lys-Val-Pro-Glu-Thr-Phe
IV. (Met)-Gly-Arg-Ser-(His)-Phe-Leu-(Cys)-(Thr)-Phe-Thr-Phe-Asn-(Ser)-Asn-(Asn)-(Lys)-(Glu)-Tyr
V. (Met)-Ala-(Trp)-Phe-Thr-Pro-Val-Gly-Leu-Ala-Val-Asp-Thr-Pro.

It is believed these sequences appear, in the order above, in the VP-1 protein.

VP-1 may be used as a vaccine when placed in a physiologically acceptable carrier, e.g., saline, to induce neutralizing antibodies when administered to a susceptible mammalian species, e.g. rats, in an amount of from about 5 to about 150 μg per dose, preferably from about 5 to about 50 μg per dose. One or more doses may be administered to produce effective protection from HAV diseases. The vaccine may be administered by injection, preferably intramuscularly.

To provide monoclonal antibodies to HAV, mammalian spleen cells typically obtained, e.g., from mice or rats, and immunized with purified HAV or VP-1 either in vivo or in vitro are fused to a mammalian myeloma cell line, typically but not necessarily from the same species used to provide the spleen cells. Hybridoma cells which result are selected for ability to make antibodies which bind HAV and neutralize the HAV infectivity as determined by an in vitro assay. The selected hybridoma cells are subcloned to provide monoclonal cell lines which produce neutralizing antibodies to HAV. Fab fragments are prepared from the purified monoclonal antibodies by standard procedures (papain digestion) and are chemically crosslinked to whole HAV. The neutralizing monoclonal antibodies are bound most specifically to the VP-1 of HAV as analyzed by gels following the crosslinking. These monoclonal antibodies can be used in a rapid diagnostic test to measure the presence of antibodies to HAV and can also measure the presence of neutralizing antibodies. Immune sera from infected animals or humans reacts with denatured VP-1 when analyzed in standard western blot or immuno blot analyses (i.e. following gel separation of HAV proteins and transfer to nitrocellulose paper).

The following examples illustrate the present invention without, however, limiting the same thereto.

EXAMPLE 1

Growth and Purification of Hepatitis A Virus

Hepatitis A virus was grown in a continuous monkey kidney cell line using the following procedure which is based on that described in U.S. Pat. No. 4,164,566.

HAV was isolated after 21 to 28 days of growth from roller bottle infected cultures of continuous monkey kidney cell line, LLC-MK2, by scraping the cells off the surface of the culture bottle and then collecting the cells by centrifugation (800×g, 10 minutes, 4° C.). The cell pellet was then resuspended in lysis buffer (10 mM Tris-HCl, pH 7.5; 10 mM NaCl; 1.5 mM $MgCl_2$; 1% polyoxyethylene(9)octaphenol; using 5 ml of buffer per pellet of two 850 cc roller bottles. The cell lysates were then sonicated for 20 seconds using a high setting on an ultrasonics sonicator and then incubated on ice for 10 minutes. Sonication was repeated for 20 seconds at the same setting. The cells were then incubated on ice for a further 20 minutes. Cell debris was pelleted by centrifugation at 10,000×g for 20 minutes at 10° C. The supernatant liquid was then carefully removed and sodium sarkosyl (SLS) was added to a final concentration of 0.5% from a 20% stock solution.

The viral-containing supernatant liquid was then incubated for 30 minutes at 37° C. followed by sonication for 10 seconds as above. The viral-containing supernatant liquid was then layered gently with a pipette over a sucrose shelf in a polycarbonate centrifuge tube.

The sucrose shelf contained 20% sucrose (RNase free) dissolved in 0.1% SLS and 10 mM Tris-HCl, pH 7.4; 150 mM NaCl; 1.0 mM EDTA (TNE). Typically the viral-containing supernatant liquid of 40 ml was layered over a sucrose shelf of 30 ml in a polycarbonate tube of 70 ml for the Beckman T-45 rotor and was then centrifuged for 20 hours at 23,000 rpm at 4° C.

Following centrifugation, the supernatant liquid was removed and the viral pellet was resuspended in 0.5% SLS in TNE and then sonicated as described above for 10 seconds.

The virus was incubated for 30 minutes at 37° C. and then sonicated for another 10 seconds as above. The virus then was layered onto a 25% to 45% preformed linear cesium chloride gradient and centrifuged for 60 hours at 40,000 rpm and 8° C. (100 ml of gradient for virus from 10 roller bottles in Beckman type 45 rotor; cesium chloride solution made in TNE and 0.1% SLS).

Fractions, 2.5 ml, were collected from the bottom of the gradient and assayed for hepatitis A viral antigen by RIA assay and the refractive index was determined to localize the infectious HAV peak at 1.34 g/ml. The peak was pooled (from 1.33 to 1.35 g/ml), diluted 20 fold with 0.1% SLS in TNE and pelleted by centrifugation at 40,000 rpm for 10 hours at 4° C. in Beckman T-45 rotor. The final viral pellet was dissolved in TNE with 0.1% SLS and the concentration was determined by RIA for viral antigen.

EXAMPLE 2

Radioactive Labelling of Hepatitis A Virus

Purified HAV was iodinated in several different experiments using either chloramine T or a lactoperoxidase system. By either of these procedures the VP-1 of HAV became more highly labelled than VP-2 or VP-3.

Typically for the chloramine T reaction, 5 to 20 micrograms of HAV isolated from CsCl gradients as described in Example 1 were labelled in a 60 second reaction with chloramine T (25 micrograms) using a sodium phosphate buffer (0.5 M) and 1.0 mCi of $I^{125}$ iodine in a total reaction volume of 0.1 ml. Sodium bisulfite (40 micrograms/0.1 ml) was added to end the reaction. The $I^{125}$ labelled HAV was then separated from the unreacted $I^{125}$ iodine by chromatography on a cross-linked dextran (Sephadex G-100) column (14 ml; 1.3×15 cm: width×height). The void volume fractions, containing the labelled virions, were analyzed by sodium dodecyl sulfate polyacrylamide gel electrophoresis (SDS-PAGE) using the Laemmli et al. discontinuous gel system (Nature: London, 277: 680–685, 1970), with the following modifications: a separating layer of 15% acrylamide-3.5 M urea and a 5% acrylamide-3.5 M urea stacking layer were utilized to resolve the major structural HAV proteins. The major bands, as resolved by coomassie blue or silver nitrate staining were at 33,000 d (VP-1); 29,000 d (VP-2); and 27,000 d (VP-3) and were present in approximately equal amounts. Other minor bands are sometimes found migrating in the region 28 to 30 kd and at 24 to 26 kd and at higher molecular weight regions (>60 kd). Although the major structural HAV proteins were present in roughly equal amounts on the basis of protein concentration, it was readily apparent that VP-1 is much more highly labelled by $I^{125}$ than either VP-2 or VP-3. (VP-3 was more highly labelled than VP-2.)

The second labelling procedure utilized the enzyme lactoperoxidase to radioactively label intact HAV with $I^{125}$ iodine. Since this enzyme should not penetrate the intact virion particle, only those proteins on the surface should be accessible to labelling. For this reaction 10 μg of purified HAV was lyophilized and then dissolved in 0.2 M sodium acetate buffer (pH 5.6) to a concentration of 10 μg/75 μl. One hundred μg of lactoperoxidase containing 6–8 units of enzyme activity and dissolved in sodium acetate buffer (pH 5.6) was added to the HAV along with 1 mCi of $I^{125}$ iodine. To initiate the reaction, 10 μl of a 1:3600 dilution of 50% $H_2O_2$ ($H_2O$ as diluent) was added and the mixture was incubated for 5 minutes. $H_2O_2$ (10 μl) was added 3 more times followed by 5-minute incubation periods after each addition. To end the reaction, 300 μl of NaI (10 mg/ml) was added and the labelled material was chromatographed on a cross-linked agarose (Sepharose CL6B) column to separate the $I^{125}$ HAV from radioactively labelled lactoperoxidase and free iodine. When the labelled HAV was analyzed on SDS-PAGE, again it appeared that the 33 kd protein (VP-1) was much more extensively labelled than either the 29 or 27 kd proteins.

These two different labelling procedures both indicate that the VP-1 is the most accessible protein for radiolabelling from the surface of the virus.

EXAMPLE 3

Isolation and Characterization of Viral Proteins

The 33 kd protein, VP-1, was isolated from HAV by first solubilizing the virus in sample buffer (as described by Laemmli, op. cit. in Example 2) and separating the individual viral proteins on a polyacrylamide gel as described in Example 2. Following electrophoresis the VP-1 was isolated from the gel by the following procedure which is based on that described in Hunkapiller et al., p. 227–236, Methods in Enzymology, Vol. 91, Academic Press, New York, N.Y 1983.

The VP-1 was localized in unfixed gels after electrophoresis by coelectrophoresing $I^{125}$ labelled HAV with unlabelled HAV and then exposing the gels to X-ray film to determine the location of each protein. The gel bands containing VP-1 were sliced from the gel with a disposable razor blade and incubated in 10 mM ammonium bicarbonate (AB), 2.0% SDS, 1.5 mM dithiothreitol for 2 hours at room temperature or 4° C. overnight. The VP-1 was then electroeluted from the gel slices and the incubation buffer by loading both into a sample cup for the ISCO Model 1750 Concentrator and electrophoresing for 4 to 5 hours at 3 watts/sample. Fifty mM AB, 0.1% SDS was used in the electrode and inner chambers. Loading, electrophoresis and unloading of the samples was as described in the manual for this instrument. Following electroelution, VP-1 was dialyzed against $dH_2O$, with 4 changes of $dH_2O$ over a 24 hour period (approximately 1 ml of VP-1 solution per 500 ml of $dH_2O$) VP-1 was then dried and either analyzed for purity (on SDS gels, as described in Example 2), or analyzed for amino acid concentration, or subjected to sequence analysis.

Amino acid concentrations were determined after a 20 hour hydrolysis of the VP-1 with 6 M HCl and were performed on a Beckman Model 121 analyzer as described in Poe et al. (J. Biol. Chem. 258:2209–2216, 1983) and Spiess et al. (Proc. Natl. Acad. Sci. USA, 76:2974–2978, 1979). The amino acid concentrations are indicated in Table 1.

TABLE I

Amino Acid Concentrations of Acid Hydrolyzed VP-1 of HAV

| Amino Acid | Experiment No. 1 (%) | Experiment No. 2 (%) |
|---|---|---|
| Glycine | 28.80 | 22.32 |
| Serine | 10.25 | 9.58 |
| Glutamic Acid and/or Glutamine | 9.73 | 8.73 |
| Aspartic Acid and/or Asparagine | 7.97 | 9.23 |
| Alanine | 6.36 | 6.90 |
| Threonine | 5.22 | 7.87 |
| Leucine | 5.28 | 6.85 |
| Valine | 4.32 | 5.17 |
| Lysine | 4.13 | 3.96 |
| Proline | 3.54 | 5.09 |
| Phenylalanine | 3.29 | 4.16 |
| Arginine | 3.93 | 2.26 |
| Isoleucine | 2.25 | 3.34 |
| Tyrosine | 2.72 | 2.41 |
| Histidine | 1.47 | 1.68 |
| Methionine | 0.74 | 0.48 |

For sequence analyses, the VP-1 was cleaved with cyanogen bromide since preliminary experiments indicated that this viral protein appeared to have a blocked amino terminus. VP-1, 10 to 40 μg, was dissolved in 70% formic acid, approximately 1 ml, and cyanogen bromide was added at a 40-fold excess by weight and incubated with the virus for 16 hours at room temperature. The cleaved protein was then subjected to sequence analyses on a gas-liquid solid phase sequenator as described in Hewick et al. (J. Biol. Chem. 256:7990–7997, 1981). The following amino acid sequence data were obtained, respectively, except for those amino acid residues shown in parenthesis which are inferred from the nucleotide sequence:

Sequence

I. Val-Gly-Asp-Asp-Ser-Gly-Gly-Phe-(Ser)-Thr-Thr

II. (Met)-Lys-Asp-Leu-Lys-Gly-Lys-Ala-Asn-Arg-Gly-Lys

III. (Met)-(Asp)-Val-Ser-Gly-Val-Gln-Ala-Pro-Val-Gly-Ala-Ile-Thr-Thr-Ile-Glu-Asp-Pro-Ala-Leu-Ala-Lys-Lys-Val-Pro-Glu-Thr-Phe

IV. (Met)-Gly-Arg-Ser-(His)-Phe-Leu-(Cys)-(Thr)-Phe-Thr-Phe-Asn-(Ser)-Asn-(Asn)-(Lys)-(Glu)-Tyr

V. (Met)-Ala-(Trp)-Phe-Thr-Pro-Val-Gly-Leu-Ala-Val-Asp-Thr-Pro

It is believed these sequences appear, in the order above, in the VP-1 protein, the protein starting with the Val of Sequence I.

The sequence data were obtained by comparing the raw sequentor data to nucleotide sequences obtained by DNA sequencing of cDNA copies of the HAV genome. This latter work is described and claimed in copending U.S. Ser. No. 585,818, filed concurrently with this C-I-P, inventors Linemeyer, Menke, Mitra, and Reuben, assigned to the same assignee, the specification of which is incorporated by reference. The partial nucleotide sequence of HAV, including the nucleotide sequence of the VP-1 genome, and its corresponding amino acid sequence follows:

| | | | | | | | 28 | | | | | | |
|---|---|---|---|---|---|---|---|---|---|---|---|---|---|
| ATG | TGT | GGG | ACG | ?QQ | ACT | TTG | CAG | TGT | AAA | CTT | GGC | TCT | CAT | GAA |
| MET | Cys | Gly | Thr | | Thr | Leu | Gln | Cys | Lys | Leu | Gly | Ser | His | Glu |

| | | 55 | | | | | | | | | 82 | | | |
|---|---|---|---|---|---|---|---|---|---|---|---|---|---|---|
| CCT | CTT | TGA | TCT | TQC | ACA | AGG | GGT | AGG | CTA | CGG | GTG | AAA | CCT | CTT |
| Pro | Leu | . | Ser | | Thr | Arg | Gly | Arg | Leu | Arg | Val | Lys | Pro | Leu |

| | | | | | 109 | | | | | | | | | 136 |
|---|---|---|---|---|---|---|---|---|---|---|---|---|---|---|
| AGG | CTA | ATA | CTT | CTA | TGA | AGA | GAT | GQT | TTG | GAT | AGG | GCA | ACA | GCG |
| Arg | Leu | Ile | Leu | Leu | . | Arg | Asp | | Leu | Asp | Arg | Ala | Thr | Ala |

| | | | | | | | 163 | | | | | | | |
|---|---|---|---|---|---|---|---|---|---|---|---|---|---|---|
| GCG | GAT | ATT | GGT | GAG | TTG | TTA | AGA | CAA | AAA | CCA | TTC | AAC | GCC | GGA |
| Ala | Asp | Ile | Gly | Glu | Leu | Leu | Arg | Gln | Lys | Pro | Phe | Asn | Ala | Gly |

| | | 190 | | | | | | | | | 217 | | | |
|---|---|---|---|---|---|---|---|---|---|---|---|---|---|---|
| GGA | CTG | GCT | CTC | ATC | CAG | TGG | ATG | CAT | TGA | GTG | GAT | TGA | TTG | TCA |
| Gly | Leu | Ala | Leu | Ile | Gln | Trp | MET | His | . | Val | Asp | . | Leu | Ser |

| | | | | 244 | | | | | | | | | | 271 |
|---|---|---|---|---|---|---|---|---|---|---|---|---|---|---|
| GGG | CTG | TQT | CTA | GGT | TTA | ATC | TCA | GAC | CTC | TCT | GTG | CTT | AGG | GCA |
| Gly | Leu | | Leu | Gly | Leu | Ile | Ser | Asp | Leu | Ser | Val | Leu | Arg | Ala |

| | | | | | | 298 | | | | | | | | |
|---|---|---|---|---|---|---|---|---|---|---|---|---|---|---|
| AAC | ACC | ATT | TGG | CCT | TAA | ATG | GGA | TCC | TGT | GAG | AGG | GGG | TCC | CTC |
| Asn | Thr | Ile | Trp | Pro | . | MET | Gly | Ser | Cys | Glu | Arg | Gly | Ser | Leu |

| | | 325 | | | | | | | | | 352 | | | |
|---|---|---|---|---|---|---|---|---|---|---|---|---|---|---|
| CAT | TGA | CAG | CTG | GAC | TGT | TCT | TTG | GGG | CCT | TAT | GTG | GTG | TTT | GCC |
| His | . | Gln | Leu | Asp | Cys | Ser | Leu | Gly | Pro | Tyr | Val | Val | Phe | Ala |

| | | | | 379 | | | | | | | | | | 406 |
|---|---|---|---|---|---|---|---|---|---|---|---|---|---|---|
| TCT | GAG | GTA | CTC | AGG | GGC | JTT | TAG | GTT | TTT | CCT | CAT | TCT | TAA | ACA |
| Ser | Glu | Val | Leu | Arp | Gly | | . | Val | Phe | Pro | His | Ser | . | Thr |

| | | | | | | | 433 | | | | | | | |
|---|---|---|---|---|---|---|---|---|---|---|---|---|---|---|
| ATA | ATG | AAT | ATG | TCC | AAA | CAA | GGA | ATT | TTC | CAG | ACT | GTC | GGG | AGT |
| Ile | MET | Asn | MET | Ser | Lys | Gln | Gly | Ile | Phe | Gln | Thr | Val | Gly | Ser |

| | | 460 | | | | | | | | | 487 | | | |
|---|---|---|---|---|---|---|---|---|---|---|---|---|---|---|
| GGC | CTT | GAC | CAC | ATC | CTG | TCT | TTG | GCA | GAT | ATT | GAG | GAA | GAG | CAA |
| Gly | Leu | Asp | His | Ile | Leu | Ser | Leu | Ala | Asp | Ile | Glu | Glu | Glu | Gln |

| | | | | 514 | | | | | | | | | | 541 |
|---|---|---|---|---|---|---|---|---|---|---|---|---|---|---|
| ATG | ATT | CAG | TCC | GTT | GTT | AGG | ACT | GCA | GTG | ACT | GGT | GCT | TCT | TAT |

-continued

| | | | | | | | | | | | | |
|---|---|---|---|---|---|---|---|---|---|---|---|---|
| MET | Ile | Gln | Ser | Val | Val | Arg | Thr | Ala | Val | Thr | Gly | Ala | Ser | Tyr |

| | | | | | | | 568 | | | | | |
|---|---|---|---|---|---|---|---|---|---|---|---|---|
| TTT | ACT | TCT | GTG | GAC | CAA | TCT | TCA | GTT | CAT | ACT | GCT | GAG | GTT | GGC |
| Phe | Thr | Ser | Val | Asp | Gln | Ser | Ser | Val | His | Thr | Ala | Glu | Val | Gly |

| | | 595 | | | | | | | | 622 | | |
|---|---|---|---|---|---|---|---|---|---|---|---|---|
| TTA | CAT | CAA | ATT | GAA | CCC | TTG | AAA | ACC | TCT | GTT | GAT | AAA | CCT | NGT |
| Leu | His | Gln | Ile | Glu | Pro | Leu | Lys | Thr | Ser | Val | Asp | Lys | Pro | |

| | | | | 649 | | | | | | | | 676 |
|---|---|---|---|---|---|---|---|---|---|---|---|---|
| TCT | AAG | AAG | ACT | CAG | GGG | GAG | AAG | TTT | TTC | CTG | ATT | CAT | TCT | GCT |
| Ser | Lys | Lys | Thr | Gln | Gly | Glu | Lys | Phe | Phe | Leu | Ile | His | Ser | Ala |

| | | | | | | | 703 | | | | | |
|---|---|---|---|---|---|---|---|---|---|---|---|---|
| GAT | TGG | CTC | ACT | ACA | CAT | GCT | CTA | TTT | CAT | GAA | GTT | GCA | AAA | TTG |
| Asp | Trp | Leu | Thr | Thr | His | Ala | Leu | Phe | His | Glu | Val | Ala | Lys | Leu |

| | | 730 | | | | | | | | 757 | | |
|---|---|---|---|---|---|---|---|---|---|---|---|---|
| GAC | GTG | GTG | AAA | TTA | TTG | TAT | AAT | GAG | CAG | TTT | GCC | GTC | CAA | GGT |
| Asp | Val | Val | Lys | Leu | Leu | Tyr | Asn | Glu | Gln | Phe | Ala | Val | Gln | Gly |

| | | | | 784 | | | | | | | | 811 |
|---|---|---|---|---|---|---|---|---|---|---|---|---|
| TTG | TTG | AGA | TAC | CAC | ACA | TAT | GCA | AGA | TTT | GGC | ATT | GAG | ATT | CAA |
| Leu | Leu | Arg | Tyr | His | Thr | Tyr | Ala | Arg | Phe | Gly | Ile | Glu | Ile | Gln |

| | | | | | | | 838 | | | | | |
|---|---|---|---|---|---|---|---|---|---|---|---|---|
| GTT | CAG | ATA | AAT | CCC | ACA | CCC | TTT | CAG | CAA | GGG | GGG | CTA | ATT | TGT |
| Val | Gln | Ile | Asn | Pro | Thr | Pro | Phe | Gln | Gln | Gly | Gly | Leu | Ile | Cys |

| | | 865 | | | | | | | | 892 | | |
|---|---|---|---|---|---|---|---|---|---|---|---|---|
| GCT | ATG | GTT | CCT | AGT | GAC | CAA | AGT | TAT | GGT | TCG | ATA | GCA | TCC | TTG |
| Ala | MET | Val | Pro | Ser | Asp | Gln | Ser | Tyr | Gly | Ser | Ile | Ala | Ser | Leu |

| | | | | 919 | | | | | | | | 946 |
|---|---|---|---|---|---|---|---|---|---|---|---|---|
| ACT | GTT | TAT | CCT | CAT | GGT | TTG | TTA | AAT | TGC | AAC | ATT | AAC | AAT | GTG |
| Thr | Val | Tyr | Pro | His | Gly | Leu | Leu | Asn | Cys | Asn | Ile | Asn | Asn | Val |

| | | | | | | | 973 | | | | | |
|---|---|---|---|---|---|---|---|---|---|---|---|---|
| GTT | AGA | ATA | AAG | GTT | CCA | TTT | ATT | TAT | ACT | AGA | GGT | GCT | TAT | CAC |
| Val | Arg | Ile | Lys | Val | Pro | Phe | Ile | Tyr | Thr | Arg | Gly | Ala | Tyr | His |

| | 1000 | | | | | | | | | 1027 | | |
|---|---|---|---|---|---|---|---|---|---|---|---|---|
| TTT | AAG | GAT | CCA | CAG | TAT | CCA | GTT | TGG | GAA | TTA | ACA | ATC | AGA | GTT |
| Phe | Lys | Asp | Pro | Gln | Tyr | Pro | Val | Trp | Glu | Leu | Thr | Ile | Arg | Val |

| | | | | 1054 | | | | | | | | 1081 |
|---|---|---|---|---|---|---|---|---|---|---|---|---|
| TGG | TCA | GAG | TTG | AAT | ATT | GGA | ACA | GGA | ACT | TCA | GCT | TAC | ACT | TCA |
| Trp | Ser | Glu | Leu | Asn | Ile | Gly | Thr | Gly | Thr | Ser | Ala | Tyr | Thr | Ser |

| | | | | | | | 1108 | | | | | |
|---|---|---|---|---|---|---|---|---|---|---|---|---|
| CTT | AAT | GTT | TTA | GCT | AGG | TTT | ACA | GAT | TTG | GAG | TTA | CAT | GGA | TTA |
| Leu | Asn | Val | Leu | Ala | Arg | Phe | Thr | Asp | Leu | Glu | Leu | His | Gly | Leu |

| | | 1135 | | | | | | | | 1162 | | |
|---|---|---|---|---|---|---|---|---|---|---|---|---|
| ACT | CCT | CTT | TCT | ACA | CAG | ATG | ATG | AGA | AAT | GAA | TTT | AGA | GTT | AGT |
| Thr | Pro | Leu | Ser | Thr | Gln | MET | MET | Arg | Asn | Glu | Phe | Arg | Val | Ser |

| | | | | 1189 | | | | | | | | 1216 |
|---|---|---|---|---|---|---|---|---|---|---|---|---|
| ACT | ACT | GAA | AAT | GTT | GTA | AAT | TTG | TCG | AAT | TAT | GAA | GAT | GCA | AGG |
| Thr | Thr | Glu | Asn | Val | Val | Asn | Leu | Ser | Asn | Tyr | Glu | Asp | Ala | Arg |

| | | | | | | | 1243 | | | | | |
|---|---|---|---|---|---|---|---|---|---|---|---|---|
| GCA | AAA | ATG | TCT | TTT | GCT | TTG | GAT | CAG | GAA | GAT | TGG | AAG | TCT | GAT |
| Ala | Lys | MET | Ser | Phe | Ala | Leu | Asp | Gln | Glu | Asp | Trp | Lys | Ser | Asp |

| | | 1270 | | | | | | | | 1297 | | |
|---|---|---|---|---|---|---|---|---|---|---|---|---|
| CCT | TCC | CAA | GGT | GGT | GGA | ATT | AAA | ATT | ACT | CAT | TTT | ACT | ACC | TGG |
| Pro | Ser | Gln | Gly | Gly | Gly | Ile | Lys | Ile | Thr | His | Phe | Thr | Thr | Trp |

| | | | | 1324 | | | | | | | | 1351 |
|---|---|---|---|---|---|---|---|---|---|---|---|---|
| ACA | TCC | ATT | CCA | ACC | TTA | GCT | GCT | CAG | TTT | CCA | TTC | AAT | GCT | TCA |
| Thr | Ser | Ile | Pro | Thr | Leu | Ala | Ala | Gln | Phe | Pro | Phe | Asn | Ala | Ser |

| | | | | | | | 1378 | | | | | |
|---|---|---|---|---|---|---|---|---|---|---|---|---|
| GAT | TCG | GTT | GGA | CAA | CAA | ATT | AAA | GTT | ATT | CCA | GTG | GAC | CCA | TAT |
| Asp | Ser | Val | Gly | Gln | Gln | Ile | Lys | Val | Ile | Pro | Val | Asp | Pro | Tyr |

| | | 1405 | | | | | | | | 1432 | | |
|---|---|---|---|---|---|---|---|---|---|---|---|---|
| TTT | TTC | CAG | ATG | ACA | AAC | ACC | AAT | CCT | GAT | CAA | AAG | TGT | ATA | ACT |
| Phe | Phe | Gln | MET | Thr | Asn | Thr | Asn | Pro | Asp | Gln | Lys | Cys | Ile | Thr |

1459                                                                     1486

-continued

| | | | | | | | | | | | | | |
|---|---|---|---|---|---|---|---|---|---|---|---|---|---|
| GCC | TTG | GCT | TCT | ATT | TGT | CAG | ATG | TTT | TGC | TTT | TGG | AGG | GGA | GAT |
| Ala | Leu | Ala | Ser | Ile | Cys | Gln | MET | Phe | Cys | Phe | Trp | Arg | Gly | Asp |

| | | | | | | | 1513 | | | | | | |
|---|---|---|---|---|---|---|---|---|---|---|---|---|---|
| CTT | GTT | TTT | GAT | TTT | CAG | GTT | TTT | CCA | ACC | AAA | TAT | CAT | TCA | GGT |
| Leu | Val | Phe | Asp | Phe | Gln | Val | Phe | Pro | Thr | Lys | Tyr | His | Ser | Gly |

| | | 1540 | | | | | | | | | 1567 | | |
|---|---|---|---|---|---|---|---|---|---|---|---|---|---|
| AGG | TTG | TTG | TTT | TGC | TTT | GTT | CCT | GGG | AAT | GAG | TTG | ATA | GAT | GTT |
| Arg | Leu | Leu | Phe | Cys | Phe | Val | Pro | Gly | Asn | Glu | Leu | Ile | Asp | Val |

| | | | | 1594 | | | | | | | | | 1621 |
|---|---|---|---|---|---|---|---|---|---|---|---|---|---|
| ACT | GGA | ATC | ACA | TTA | AAA | CAG | GCA | ACC | ACT | GCT | CCT | TGT | GCA | GTG |
| Thr | Gly | Ile | Thr | Leu | Lys | Gln | Ala | Thr | Thr | Ala | Pro | Cys | Ala | Val |

| | | | | | | 1648 | | | | | | | |
|---|---|---|---|---|---|---|---|---|---|---|---|---|---|
| ATG | GAC | ATT | ACA | GGA | GTG | CAG | TCA | ACC | TTG | AGA | TTT | CGT | GTT | CCT |
| MET | Asp | Ile | Thr | Gly | Val | Gln | Ser | Thr | Leu | Arg | Phe | Arg | Val | Pro |

| | | 1675 | | | | | | | | | 1702 | | |
|---|---|---|---|---|---|---|---|---|---|---|---|---|---|
| TGG | ATT | TCT | GAT | ACA | CCC | TAT | CGA | GTG | AAT | AGG | TAC | ACG | AAG | TCA |
| Trp | Ile | Ser | Asp | Thr | Pro | Tyr | Arg | Val | Asn | Arg | Tyr | Thr | Lys | Ser |

| | | | | 1729 | | | | | | | | | 1756 |
|---|---|---|---|---|---|---|---|---|---|---|---|---|---|
| GCA | CAT | CAA | AAA | GGT | GAG | TAT | ACT | GCC | ATT | GGG | AAG | CTT | ATT | GTG |
| Ala | His | Gln | Lys | Gly | Glu | Tyr | Thr | Ala | Ile | Gly | Lys | Leu | Ile | Val |

| | | | | | | | 1763 | | | | | | |
|---|---|---|---|---|---|---|---|---|---|---|---|---|---|
| TAT | TGT | TAT | AAT | AGG | CTG | ACT | TCT | CCT | TCT | AAT | GTT | GCT | TCT | CAT |
| Tyr | Cys | Tyr | Asn | Arg | Leu | Thr | Ser | Pro | Ser | Asn | Val | Ala | Ser | His |

| | | 1810 | | | | | | | | | 1837 | | |
|---|---|---|---|---|---|---|---|---|---|---|---|---|---|
| GTT | AGA | GTT | AAT | GTT | TAT | CTT | TCA | GCA | ATT | AAT | TTG | GAA | TGT | TTT |
| Val | Arg | Val | Asn | Val | Tyr | Leu | Ser | Ala | Ile | Asn | Leu | Glu | Cys | Phe |

| | | | | 1864 | | | | | | | | | 1891 |
|---|---|---|---|---|---|---|---|---|---|---|---|---|---|
| GCT | CCT | CTT | TAT | CAT | GCT | ATG | GAT | GTT | ACC | ACA | CAG | GTT | GGA | GAT |
| Ala | Pro | Leu | Tyr | His | Ala | MET | Asp | Val | Thr | Thr | Gln | Val | Gly | Asp |
| | | | | | | | | | | | | I | | |

| | | | | | | 1918 | | | | | | | |
|---|---|---|---|---|---|---|---|---|---|---|---|---|---|
| GAT | TCA | GGA | GGT | TTT | TCA | ACA | ACA | GTT | TCG | ACA | GAG | CAG | AAT | GTT |
| Asp | Ser | Gly | Gly | Phe | Ser | Thr | Thr | Val | Ser | Thr | Glu | Gln | Asn | Val |

| | | 1945 | | | | | | | | | 1972 | | |
|---|---|---|---|---|---|---|---|---|---|---|---|---|---|
| CCT | GAT | CCC | CAA | GTT | GGT | ATA | ACA | ACT | ATG | AAG | GAC | CTG | AAA | GGG |
| Pro | Asp | Pro | Gln | Val | Gly | Ile | Thr | Thr | MET | Lys | Asp | Leu | Lys | Gly |
| | | | | | | | | | II | | | | | |

| | | | | 1999 | | | | | | | | | 2026 |
|---|---|---|---|---|---|---|---|---|---|---|---|---|---|
| AAA | GCC | AAT | AGG | GGA | AAG | ATG | GAT | GTT | TCA | GGA | GTG | CAA | GCA | CCT |
| Lys | Ala | Asn | Arp | Gly | Lys | MET | Asp | Val | Ser | Gly | Val | Gln | Ala | Pro |
| | | | | | | III | | | | | | | | |

| | | | | | | | 2053 | | | | | | |
|---|---|---|---|---|---|---|---|---|---|---|---|---|---|
| GTG | GGA | GCT | ATC | ACA | ACA | ATT | GAG | GAT | CCA | GCA | TTA | GCA | AAG | AAA |
| Val | Gly | Ala | Ile | Thr | Thr | Ile | Glu | Asp | Pro | Ala | Leu | Ala | Lys | Lys |

| | | 2080 | | | | | | | | | 2107 | | |
|---|---|---|---|---|---|---|---|---|---|---|---|---|---|
| GTA | CCT | GAA | ACG | TTT | CCT | GAA | TTG | AAG | CCT | GGA | GAG | TCT | AGA | CAT |
| Val | Pro | Glu | Thr | Phe | Pro | Glu | Leu | Lys | Pro | Gly | Glu | Ser | Arg | His |

| | | | | 2134 | | | | | | | | | 2161 |
|---|---|---|---|---|---|---|---|---|---|---|---|---|---|
| ACA | TCA | GAT | CAC | ATG | TCT | ATT | TAT | AAA | TTC | ATG | GGA | AGG | TCT | CAT |
| Thr | Ser | Asp | His | MET | Ser | Ile | Tyr | Lys | Phe | MET | Gly | Arp | Ser | His |
| | | | | | | | | | | IV | | | | |

| | | | | | | 2188 | | | | | | | |
|---|---|---|---|---|---|---|---|---|---|---|---|---|---|
| TTT | TTG | TGT | ACT | TTT | ACC | TTC | AAT | TCA | AAT | AAT | AAA | GAG | TAC | ACA |
| Phe | Leu | Cys | Thr | Phe | Thr | Phe | Asn | Ser | Asn | Asn | Lys | Glu | Tyr | Thr |

| | | 2215 | | | | | | | | | 2242 | | |
|---|---|---|---|---|---|---|---|---|---|---|---|---|---|
| TTT | CCA | ATA | ACC | TTG | TCT | TCG | ACT | TCT | AAT | CCT | CCT | CAT | GGT | TTA |
| Phe | Pro | Ile | Thr | Leu | Ser | Ser | Thr | Ser | Asn | Pro | Pro | His | Gly | Leu |

| | | | | 2269 | | | | | | | | | 2296 |
|---|---|---|---|---|---|---|---|---|---|---|---|---|---|
| CCA | TCA | ACA | TTA | AGG | TGG | TTC | TTC | AAT | CTG | TTT | CAG | TTG | TAT | AGA |
| Pro | Ser | Thr | Leu | Arp | Trp | Phe | Phe | Asn | Leu | Phe | Gln | Leu | Tyr | Arg |

| | | | | | | | 2323 | | | | | | |
|---|---|---|---|---|---|---|---|---|---|---|---|---|---|
| GGA | CCA | TTG | GAT | TTG | ACA | ATT | ATC | ATC | ACA | GGA | GCT | ACT | GAT | GTG |

-continued

| | | | | | | | | | | | | | |
|---|---|---|---|---|---|---|---|---|---|---|---|---|---|
| Gly | Pro | Leu | Asp | Leu | Thr | Ile | Ile | Ile | Thr | Gly | Ala | Thr | Asp | Val |
| | | 2350 | | | | | | | | | 2377 | | | |
| GAT | GGA | ATG | GCC | TGG | TTT | ACT | CCA | GTA | GGC | CTT | GCT | GTT | GAC | ACC |
| Asp | Gly | MET | Ala | Trp | Phe | Thr | Pro | Val | Gly | Leu | Ala | Val | Asp | Thr |
| | | V | | | | | | | | | | | | |
| | | | | 2404 | | | | | | | | | | 2431 |
| CCA | TGG | GTG | GAA | AAG | GAA | TCA | GCT | TTG | TCT | ATT | GAT | TAT | AAA | ACT |
| Pro | Trp | Val | Glu | Lys | Glu | Ser | Ala | Leu | Ser | Ile | Asp | Tyr | Lys | Thr |
| | | | | | | | 2458 | | | | | | | |
| GCC | CTT | GGA | GCT | GTT | AGA | TTT | AAT | ACA | AGA | AGA | ACA | GGG | AAC | ATT |
| Ala | Leu | Gly | Ala | Val | Arg | Phe | Asn | Thr | Arg | Arg | Thr | Gly | Asn | Ile |
| | | 2485 | | | | | | | | | 2512 | | | |
| CAG | ATT | AGA | TTG | CCA | TGG | TAT | TCT | TAT | TTA | TAT | GCT | GTG | TCT | GGA |
| Gln | Ile | Arg | Leu | Pro | Trp | Tyr | Ser | Tyr | Leu | Tyr | Ala | Val | Ser | Gly |
| | | | | 2539 | | | | | | | | | | 2566 |
| GCA | CTG | GAT | GGC | TTG | GGA | GAT | AAG | ACA | GAT | TCT | ACA | TTT | GGA | TTG |
| Ala | Leu | Asp | Gly | Leu | Gly | Asp | Lys | Thr | Asp | Ser | Thr | Phe | Gly | Leu |
| | | | | | | 2593 | | | | | | | | |
| GTT | TCC | ATA | CAG | ATT | GCA | AAT | TAC | AAC | CAC | TCT | GAT | GAA | TAT | TTG |
| Val | Ser | Ile | Gln | Ile | Ala | Asn | Tyr | Asn | His | Ser | Asp | Glu | Tyr | Leu |
| | | 2620 | | | | | | | | | 2647 | | | |
| TCC | TTT | AGT | TGT | TAT | TTG | TCT | GTC | ACA | MAA | CAA | TCA | GAG | TTC | TAT |
| Ser | Phe | Ser | Cys | Tyr | Leu | Ser | Val | Thr | | Gln | Ser | Glu | Phe | Tyr |
| | | | | 2674 | | | | | | | | | | 2701 |
| TTT | CCT | AGA | GCT | CCA | TTA | AAT | TCA | AAT | GCT | ATG | TTG | TCC | ACT | GAG |
| Phe | Pro | Arg | Ala | Pro | Leu | Asn | Ser | Asn | Ala | MET | Leu | Ser | Thr | Glu |
| | | | | | | | 2728 | | | | | | | |
| TCT | ATG | ATG | AGT | AGA | ATT | GCA | GCT | GGA | GAC | TTG | GAG | TCA | TCA | GTG |
| Ser | MET | MET | Ser | Arg | Ile | Ala | Ala | Gly | Asp | Leu | Glu | Ser | Ser | Val |
| | | 2755 | | | | | | | | | 2782 | | | |
| GAT | GAT | CCT | AGA | TCA | GAG | GAA | GAC | AGA | AGA | TTT | GAG | AGT | CAT | ATA |
| Asp | Asp | Pro | Arg | Ser | Glu | Glu | Asp | Arg | Arg | Phe | Glu | Ser | His | Ile |
| | | | | 2809 | | | | | | | | | | 2836 |
| GAA | TGT | AGG | AAA | CCA | TAT | AAA | GAA | TTG | AGA | TTG | GAG | GTT | GGG | AAA |
| Glu | Cys | Arg | Lys | Pro | Tyr | Lys | Glu | Leu | Arg | Leu | Glu | Val | Gly | Lys |
| | | | | | | 2863 | | | | | | | | |
| CAA | AGA | CTT | AAA | TAT | GCT | CAG | GAA | GAG | TTG | TCA | AAT | GAA | GTG | CTT |
| Gln | Arg | Leu | Lys | Tyr | Ala | Gln | Glu | Glu | Leu | Ser | Asn | Glu | Val | Leu |
| | | 2890 | | | | | | | | | 2917 | | | |
| CCA | CCT | CCT | AGG | AAA | ATG | AAG | GGG | TTA | TTT | TCA | CAA | GCC | AAA | ATT |
| Pro | Pro | pro | Arg | Lys | MET | Lys | Gly | Leu | Phe | Ser | Gln | Ala | Lys | Ile |
| | | | | 2944 | | | | | | | | | | 2971 |
| TCT | CTT | TTT | TAT | ACT | GAG | GAA | CAT | GAA | ATA | ATG | AAA | TTT | LCQ | TGG |
| Ser | Leu | Phe | Tyr | Thr | Glu | Glu | His | Glu | Ile | MET | Lys | Phe | | Trp |
| | | | | | | 2998 | | | | | | | | |
| AGA | GGA | GTG | A | | | | | | | | | | | |
| Arg | Gly | Val | | | | | | | | | | | | | wherein the triplet MAA is either CAA or GAA.

Since HAV is an RNA virus it is to be understood that the foregoing nucleotides designated by the letter "T" which denotes deoxythymidine phosphate are actually uridine phosphate conventionally designated by the letter "U". The underlined and numbered sequences designate the nucleotide sequences corresponding, respectively, to the similarly numbered amino acid sequences on page 16.

EXAMPLE 4

Immunization of Mice with Purified Hepatitis A Virus

Adult BALB/C mice were injected intraperitoneally with purified whole HAV as obtained according to Example 1. Each mouse received 5 μg of purified HAV dissolved in a volume of 0.5 ml of complete Freund's adjuvant. Serum was collected from one eye of each mouse 18 days after viral injection and tested for antibody to HAV by a standard competitive RIA assay (HAVAB, Abbott), and by a neutralization assay (described below); serum collected prior to injection of the virus served as control for these analyses.

Mice that were positive for anti-HAV antibodies by both RIA (as described in Example 7) and neutralization assays (as described in Example 8) were primed 3 days prior to the cell fusion by injection of 3.5 μg of purified HAV in the tail vein (in aqueous solution, 0.2 ml/mouse). Serum collected at death from the two animals used for the cell fusion was assayed for antibody to HAV (HAVAB, Abbott) and neutralization activities and was demonstrated to be positive.

EXAMPLE 5

Production of Hybridomas by Fusion of Immune Mouse Spleen Cells with Mouse Myeloma Cells Mouse myeloma cells (SP 2/0) were grown from frozen seed stock in HT media. Each 100 ml of HT media contained 66 ml of Dulbecco's Modified Eagle's Media; 20 ml fetal calf serum (FCS); 10 ml of NCTC 109 with Eagle's balanced salts; 2 ml of 200 mM L-glutamine; 1 ml of a solution containing 408 mg hypoxanthine and 114 mg thymidine in 300 ml of distilled $H_2O$; and 1 ml of OPI stock (1.5 g cis-oxalacetic acid, 0.5 g pyruvic acid, 2000 units bovine insulin in 100 ml $H_2O$ ); and 0.2 ml of a penicillin (10,000 units/ml) and streptomycin (10,000 μg/ml) mixture. The mouse spleens from animals immunized with HAV (Example 4) were removed after cervical dislocation and placed in serumless HT media at room temperature. The spleens were placed in a plastic petri dish and the cells were teased from the spleen with a plastic scraper. The plates were washed with 5 ml of serumless HT media and the cells were pooled into a 15 ml plastic conical tube; large particles were allowed to settle for one minute. The supernatant was then transferred to a 15 ml plastic round bottom tube and the cells were pelleted by a 10 minute centrifugation, 350×g at room temperature. The supernatant was discarded and the cells were resuspended in serumless HT media (10 ml/2 spleens) and the total viable cells were determined by trypan blue exclusion.

The number of viable SP 2/0 myeloma cells was also determined and the cells were combined using one log more spleen cells than myeloma cells (i.e. into a 50 cc screw cap plastic tube were placed $2 \times 10^8$ spleen cells and $2 \times 10^7$ SP 2/0 cells). The cells were pelleted by centrifugation for 10 minutes at 350×g and then the cell pellet was resuspended in 10 ml of serumless HT media. This pelleting and resuspension-washing procedure was repeated two more times, and after the final resuspension in 10 ml of serumless HT media the cells were transferred to a 15 ml round bottom tube. The cells were pelleted at 350×g for 10 minutes.

Polyethylene glycol (PEG; molecular weight average=1000d) was liquified at 45° C. and combined with serumless HT media to a concentration of 35% PEG (vol/vol). The PEG/HT media mixture was sterilized by passing it through a 0.22 micron membrane filter fitted on the end of 3 ml syringe; the PEG was then maintained at 37° C. Dimethylsulfoxide (DMSO) was added to the PEG/media mixture to a final concentration of 5%. The PEG/DMSO/HT media mixture was added dropwise to the spleen-myeloma cell pellet, using 0.8 ml for $2 \times 10^8$ cells while gently resuspending the cells by tapping the side of the culture tube and swirling the cells. The cell pellets were centrifuged at 250×g at room temperature so that the total contact time of the cells with PEG was 6 minutes. The PEG supernatant was then aspirated off and the cells were resuspended in 10 ml of HT media. The cells were pelleted (350×g for 10 minutes) and gently resuspended in HT media to a final concentration of $3.5 \times 10^5$ myeloma cells/ml. The cells were then plated in 96 well microtiter plates using 0.1 ml/well with a pipet and incubated at 37° C. in a water-jacketed $CO_2$ incubator with 5% $CO_2$ and 96% humidity.

After 24 hours, 0.1 ml of HAT media (HT media plus aminopterin at 0.352 mg/liter) was added to each well. The wells were refed with 0.1 ml of fresh HAT media every 4 to 5 days.

Some cells from culture wells which were at a confluency of 15% or greater (usually 40 to 80%) were tested for production of antibodies to HAV by the monoclonal RIA and neutralization assays described below in Examples 7 and 8.

Those cells having high activity by the above assays were subcloned by two cycles of limiting dilutions. Four subclones were selected which had high HAV binding and neutralization activities. The purified monoclonal antibodies from these subclones were characterized as to immunoglobulin subtype and molecular weight by standard procedures. The following results were obtained:

| MONOCLONAL ANTIBODY | SUBTYPE | MOLECULAR WEIGHT (daltons) | |
|---|---|---|---|
| | | Heavy Chain | Light Chain |
| A | IgG-2a | 49,000 | 27,000 |
| B | IgG-1 | 49,000 | 27,000 |
| C | IgG-2a | 49,000 | 27,000 |
| D | IgG-2a | 49,000 | 27,000 |

EXAMPLE 6

Purification of Monoclonal Antibodies From Tissue Culture Media

The monoclonal antibodies used in crosslinking experiments, immune precipitations of labelled HAV and other experiments to identify the neutralizing sites on the virus were purified from tissue culture fluid taken from growing cultures of the hybridoma cells producing individual antibody. The following procedure was employed and is essentially that described in Emini et al. (J. Virol. 43:997–1005, 1982). Tissue culture fluid, 2 liters, from a particular hybridoma cell line were filtered through a Whatmann 4M filter paper, a glass wool containing column, and finally a column containing agarose (Sepharose 6B). The tissue culture fluid was then adjusted to a pH of 8.0 by the addition of 100 mM Tris-HCl, pH 8.0, and then passed over a protein A-Sepharose column (4 to 6 ml bed volume per 2 liters of fluid). The column was washed with 10 bed volumes of 100 mM Tris-HCl (pH 8.0). Glycine (100 mM) pH 3.0 was then added to elute the bound immunoglobulins from the column; fractions were collected with 100 mM Tris-HCl (pH 8.0) in the bottom of each tube such that the pH was changed from the acid pH of glycine to the higher pH to stabilize the antibody. Peak protein fractions from the column were pooled, dialyzed against distilled $H_2O$ and either used as whole antibody or were treated further to obtain Fab fragments.

To obtain Fab fragments of the individual monoclonal antibodies, 10 to 15 mg of the antibody purified using protein A columns, as described above, were lyophilized and then dissolved in 100 mM sodium phosphate, 10 mM cysteine, pH 7.2 (2 ml/20 mg antibody). Papain, 10–15 units per mg, was added to a ratio of 1:100, enzyme to antibody by weight. This reaction was incubated overnight for 16 hours at 37° C. and it was terminated with the addition of iodoacetamide to a final concentration of 30 mM. The digested antibody was then chromatographed over a cross-linked dextran (Sephahex G-75) column (2.5×20 cm, width×height) at 4°

C and the fractions were monitored for absorbance at 280 nm as a measure of the protein present. The second peak off the column, which contained the majority of the Fab fragments, was pooled and then passed through a protein A-sepharose column to eliminate any contaminating Fc fragments or undigested antibody which bind to the protein A column. The peak fractions of Fab fragments from the protein A column were pooled, dialyzed against distilled $H_2O$, and then lyophilized in 200 μg aliquots and stored at −80° C.

EXAMPLE 7

Radioimmunoassay to Detect Antibodies to Hepatitis A Virus

For this assay polystyrene beads, 0.6 mm diameter, were coated with antisera to detect either mouse or rat antibodies to HAV using either goat anti-mouse immunoglobulins (IgG) or goat anti-rat IgG. Coating was performed by diluting the coating antisera to at least 1:400 (up to 1:1000) in saline and incubating the beads overnight at room temperature. The beads were then washed four times with distilled $H_2O$, air dried, and stored at −20° C.

For the assay 10 to 20 μl of each sera (from mice immunized with HAV in Example 4) or monoclonal tissue culture fluid (from Example 5) was diluted to 0.2 ml with PBS (phosphate buffered saline) containing 1% BSA (bovine serum albumin) and 0.02% sodium azide and added to a well in a plastic reaction tray. One bead, coated with goat anti-mouse Ig to detect mouse antibodies (or the appropriate anti-rat sera for rat monoclonals) was added to each well and incubated with the test sera for 2 hours at 37° C.

The beads were washed 3 times with 3–5 ml quantities of water and 0.2 ml of HAV (prepared as described in Example 1) and diluted to 50 nanograms/ml in PBS with 1% BSA and 0.02% sodium azide), were added per well, and incubated overnight at room temperature. The beads were again washed 3 times with 5 ml water/wash. $I^{125}$ antibody to HAV (HAVAB, Abbott), was added (0.2 ml) and incubated 2 hours at 37° C. The beads were washed as above and counted in a gamma counter for one minute/sample.

Positive controls included rat or mouse sera from HAV-immunized animals that were shown to be positive for antibodies to HAV by the neutralization assay and HAVAB assay. Negative controls were either PBS alone or pre-immunization sera from the animals utilized for the positive sera. Each test sera or monoclonal antibody was called positive if the counts per minute exceeded 5 standard deviations greater than the mean of the negative controls.

If desired the beads may be coated directly with anti-HAV monoclonal antibody prior to addition to HAV thereby eliminating the goat anti-mouse or goat anti-rat antibody layer.

EXAMPLE 8

Neutralization Assay for Hepatitis A Virus

Newborn cynomologous monkey kidney (NBCmK) cells were set up from frozen stock cultures at a concentration of $1 \times 10^4$ cells/well in a 96 well plate using 0.2 ml/well of EMEM (Eagle Minimum Essential Medium) plus 10% FCS and incubated in a $CO_2$ water-jacketed incubator at 35° C. with 5% $CO_2$ in a humidified atmosphere for 5 to 7 days until 80 to 90% confluency was attained. LLC-MK-2, a continuous monkey kidney cell line, has also been utilized in this assay for the growth and neutralization of HAV, although the incubation times for detection of the viral growth were longer (10 to 14 days as opposed to 6 to 8 days with NBCmK cells).

The virus stock used in these assays was previously grown in the cell type to be used for the assay (i.e. NBCmK viral stock only in NBCmK cells). Although untreated HAV stock prepared by previously described procedures (U.S. Pat. No. 4,164,566) could be used in these assays, a more sensitive titer of neutralizing antibody activity can be determined with HAV treated with the detergent SLS. For this treatment, SLS from 20% stock solution was added to the stock HAV to a final concentration of 0.1%. The virus was mixed thoroughly and incubated at 37° C. for 60 minutes. The virus was dialyzed using 3 changes of phosphate buffered saline of 4 liters/change for 3 to 4 ml of HAV over a period of 36 hours. The viral solution was then removed from the dialysis bag, sterile filtered and stored in small (0.3 to 0.5 ml) aliquots at −20° C.

On the day the neutralization assay was performed, the viral stock was diluted using several 5- or 10-fold dilutions (EMEM media was used for these dilutions). Sera or tissue culture fluid containing monoclonal antibodies was added to the dilutions of HAV in either small plastic tubes or in a microtiter plate; normally 0.1 ml of each viral dilution is added and sera was added, diluted as above, from 1:4 up to 1:200 (or even higher dilutions for some hyperimmune animal sera). The mixture of virus and antisera was mixed and then incubated for 60 minutes at room temperature.

The culture media was aspirated off of the test cells and the pre-incubated virus-antibody mixture was added using separate micropipette tips for each dilution to avoid contamination. The microtiter plates of cells were rocked on a platform for 30 minutes at room temperature and then incubated in a stationary position for 3 hours at 35° C. The media was then aspirated off and fresh EMEM with 0.5% FCS, 2 mM glutamine, 50 units/ml of penicillin and 50 micrograms/ml of streptomycin was added (0.25 ml/well of a 96 well microtiter plate).

The cells were then incubated at 35° C. in a $CO_2$ water-jacketed incubator. The cells were refed on the fifth day following the infection with HAV by first removing the media by aspiration and then adding fresh EMEM with fetal calf serum, glutamine, penicillin, and streptomycin as described above.

The cells were fixed on the seventh day following infection for NBCmK cells and on the tenth to fourteenth day for LLC-MK-2 cells. For this step, the media was aspirated off and the cells were washed gently with 3 washes of 0.2 ml of PBS/wash/well. Acetone was added to fix the cells at 200 μl/well and was aspirated off very quickly so that the total contact time of acetone and cells was less than 60 seconds. The plates were air dried to remove all acetone.

$I^{125}$-labelled antibody to HAV (HAVAB, Abbott) was added to each well at 0.040 ml/well (approximately 0.15 microcuries/well). The plate was incubated for 60 minutes on a rocking platform at room temperature and then for 3 hours at 35° C. in a stationary position. The $I^{125}$ antisera was then aspirated off and the wells washed 3 times with 0.3 ml of PBS/well/wash. The plates were then washed 10 times with gently running water. After air drying the plates or quickly drying in an oven, the plates were exposed to X-ray film with an intensifying screen. This exposure was done at −70° C. and lasted from 10 hours to 3 days.

Controls included (1) uninfected cells for background labelling with $I^{125}$ antibody preparation, (2) virus dilution to which no antisera or monoclonal tissue culture fluid was added to determine the titer of the virus, and (3) pre- and post-inoculation sera from either mice, rats, marmosets or chimpanzees that had previously been shown to be negative and positive (respectively) for neutralizing antisera to HAV.

To determine the neutralizing titer of the sera or monoclonal antibodies, the titer of the untreated virus was first determined comparing the radioactive labelling (darkness of X-ray film) of the virus dilutions to the labelling of uninfected cells. Next, the highest antibody dilution that gave an inhibition of the growth of Hepatitis A (or less antigen made/well) was determined by comparing the wells that contained Hepatitis A plus the test sera or monoclonal antibodies to the viral growth with virus alone. This was done either visually or using a densitometer to scan the radioactive film to determine more accurate percentages for inhibition of growth.

Both monoclonal antibodies and sera from HAV immunized hosts were shown to have virus neutralizing activity by the foregoing assay.

EXAMPLE 9

Crosslinking Monoclonal Antibodies to HAV

Neutralizing monoclonal antibodies directed towards HAV were cross-linked to the virus by the use of the heterobifunctional crosslinker toluene-2,4-diisocyanate (TDI), with the following minor adaptations of the procedure described in Emini et al. (J. Virol. 43:997–1005, 1982). Sodium phosphate buffer (10 mM, pH 7.2) was added to dried Fab fragments of a monoclonal antibody, usually to a final concentration of 0.5 μg/μl. TDI was then added, 1.1 μl/200 μl of antibody. The antibody-Fab fragment was then incubated with the TDI at either 4° C. or at room temperature. The reaction was terminated by taking aliquots at various times, usually less than 10 minutes, and incubating these aliquots at 0° C. for 10 minutes to solidify the TDI. The TDI was removed by pelleting the solidified TDI at 2,000×g at 0° C. and then repeating the 0° C. incubation and pelleting steps. The final supernatant then was taken and HAV was added to the antibody. HAV was added either as unlabelled virus, with 3 to 5 μg/reaction, or $I^{125}$ labelled HAV, with 50,000 to 70,000 cpm per reaction, or $S^{35}$ labelled HAV, with 3000 to 7000 cpm. The virus was incubated with the antibody for 30 minutes at room temperature.

Saturated tribasic phosphate buffer was added to raise the pH to 9.6 for 10 minutes at room temperature. Saturated monobasic phosphate was then added to lower the pH to 7.0. The samples then were dialyzed against $dH_2O$ overnight with 3 changes of the water. Each sample was lyophilized to dryness and run on a polyacrylamide gel as described in Example 2. Following the electrophoresis, the gels were stained with coomassie blue (R-250, 0.2% in a 50% solution of methanol) for a 30 minute period and then destained with 15% methanol, 5% acetic acid. The gel was dried and then exposed to X-ray film for varying lengths of time. To determine the degree of crosslinking to individual proteins, a densitometer tracing of the X-ray film was performed which also gave a quantitative measure of the various viral peaks. In the case of nonradioactive HAV, the gels themselves were scanned and then dried. The monoclonal antibody was cross-linked to $I^{125}$ labelled HAV at either 4° C. or room temperature. At either temperature the antibody crosslinked to the 33 kd protein, VP-1, to a greater extent than to VP-2, a 28–29 kd protein or to VP-3, the 27 kd protein.

EXAMPLE 10

Immuno-Blot Assay of Antibodies to Hepatitis A Viral Proteins

An immuno-blot assay of antibodies to HAV was performed according to the instructions included in the Immuno-Blot test kit from Bio-Rad Laboratories using either goat anti-rabbit:horse radish peroxidase (GAR-HRP) or goat anti-mouse:horse radish peroxidase (GAM-HRP) for detecting rabbit or mouse sera respectively. Essentially HAV was electrophoresed on polyacrylamide gels as in Example 2 and then transferred onto nitrocellulose membranes (in kit) using a Hoefer Scientific Instruments TE 42 Transphor and a transfer buffer consisting of 100 mM Tris, 16 mM glycine, 20% methanol for a 4 hour transfer at an average voltage of 60. The nitrocellulose membrane was then blocked with 3% gelatin in Tris buffered saline (TBS) (20 mM Tris-HCl, pH 7.5; 500 mM NaCl) as described in the Bio-Rad manual. Strips of the nitrocellulose membrane were then incubated overnight with dilutions in the range of 1:5 to 1:25 for monoclonal tissue culture fluid and 1:100 to 1:400 for pre- and post-HAV infection sera from humans, chimpanzees, marmosets, mice, rabbits, rats and guinea pigs. After incubation, the membranes were washed first with $dH_2O$ briefly and then TTBS (TBS with 0.05% polyoxyethylene(20)sorbitan monolaurate) twice for 10 minutes each time. Chimpanzee, marmoset, and human sera samples were then incubated for 1 hour with rabbit anti-human sera diluted 1:2000 to 1:3000. After a brief washing, as described above, all samples were then incubated with the final indicator antibody: GAR-HRP for all rabbit sera and for those washed in a second antibody containing a rabbit sera or GAM-HRP for those containing mouse sera. After a 2 hour room temperature incubation, the strips of nitrocellulose were washed and the color reagents were added as described in the Bio-Rad manual to develop the reaction of antibodies to specific HAV proteins.

The post chimpanzee antisera reacted mainly with VP-1, with a lower response to VP-2 and VP-3. Nonspecific response of the pre-chimpanzee sera was noted only when the lower dilutions of the second antibody (rabbit anti-human) were used and was to all of the protein present at equal levels but was not detected at higher (1:3000) dilutions. Marmoset post-infection sera reacted strongly to both VP-1 and VP-2 and to a lesser extent to VP-3, while pre-sera did not react to any of the proteins. Human pre- and post-sera reacted in a fashion similar to the marmoset sera. Sera from mice or rabbits injected with HAV mainly reacted with VP-1, with lower responses to VP-2 and VP-3.

EXAMPLE 11

Modified Competition Assay for Antibodies to Hepatitis A Virus

For this procedure, some of the reagents and the general procedure that are used in a commercial kit for measuring antibodies to HAV (HAVAB, Abbott) were used with the modifications described below. Briefly, the tissue culture media (from hybridoma cells) or sera that was to be tested was added, normally 100 microliters, to the wells of a 20 well microtiter plate. If less than 100 microliters was used, then PBS containing 1 mg/ml BSA was added to bring the volume up to 100 microliters. To each well was then added 100 microliters of either $I^{125}$ human antibody to HAV (HAVAB, Abbott) or $I^{125}$ monoclonal antibody prepared as described in Example 13. One polystyrene bead, to which is bound HAV, was added to each well. The microtiter plate was incubated on a rocking platform for 30 minutes and then overnight at room temperature in a stationary position. The test sera or media and competing labelled antibodies were then aspirated off and the beads were washed 3 times with 2 ml of distilled $H^2O$ and then counted in a gamma counter (1 minute/sample). Controls included positive and negative human seras (HAVAB, Abbott) and the cutoff for determining whether a test sera or monoclonal antibody was positive was determined by summing the cpm for negative and positive seras and dividing by 2.

When the modified competition assay was tested using pre- and post-sera from animals (mice, marmosets, chimpanzees), the test was easily able to distinguish pre-sera as negative and post-sera as positive. When monoclonal tissue culture fluids were used in this assay some, though not all, of the monoclonals would compete with the $I^{125}$ labelled human antibody to HAV. All the positive monoclonals, including A, C and D from Example 5, compete with $I^{125}$ antibody to HAV. When these monoclonals were mixed together in combinations of two (still using a total test volume of 100 microliters), some combinations of monoclonals appeared to complement each other with a resultant greater competition while other combinations gave only the same level of competition. Apparently, those monoclonals that were enhanced by combining the two are directed to two different sites on HAV, while those that were not enhanced are to the same or similar sites on the virus.

When one of the monoclonal antibodies was labelled with $I^{125}$ and used as the competing antibody in a competition assay, such an assay system could readily detect distinct binding levels for positive and negative sera to HAV. For these analyses, various levels of human positive and negative human sera to HAV (HAVAB, Abbott) and pre- and post-seras from the injection of mice, chimpanzees, and marmosets were added to the microtiter plates as described above and 100 microliters of $I^{125}$ labelled monoclonal antibody was added to compete for the binding to the HAV coated polystyrene beads. This assay was able to detect distinct differences in the binding of negative and positive sera and the fact that the $I^{125}$ labelled antibody was a neutralizing antibody indicates that antibodies in the test sera that are competing are also to the same neutralizing site or epitope that the monoclonal is directed towards. Thus, a competitive assay using $I^{125}$ labelled neutralizing monoclonal antibodies, that includes monoclonals to at least one neutralizing site on HAV, provides a rapid assay system for determining the presence of protective or neutralizing antibodies in test sera. In contrast there is no evidence that commercially available anti-HAV antibody detecting systems which employ polycolonal anti-HAV antibodies react solely with neutralizing sites on the HAV.

EXAMPLE 12

Ascites Fluid From Animals Injected with Hybridomas Producing Monoclonal Antibodies to Hepatitis A Virus Young adult BALB/C mice were primed 2 to 5 weeks prior to injection of the hybridoma cells by an injection of 0.5 ml of pristine intraperitoneally. Hybridoma cells were diluted in EMEM and injected intraperitoneally at a level of $10^6$ to $10^7$ cells/mouse in a volume of approximately 1 ml. Although the growth of hybridoma cells can vary considerably for growth as ascites, typically the ascites fluid was collected after 10 to 14 days with a needle inserted into the peritoneal cavity. Ascites fluid was stored at 4° C. until used.

EXAMPLE 13

Radioactive Labelling of Monoclonal Antibody

Monoclonal antibody was purified from ascites fluid prepared as in Example 12, by precipitating the antibody with the addition of ammonium sulfate to a concentration of 202 milligrams/ml at 4° C. The material was pelleted at 10,000×g for 15 minutes and the pellet was dissolved in PBS and passed over a A-25 column to remove any contaminating IgM and IgA. The void volume had 1 to 2 peak protein fractions which were concentrated at 4° C. to a protein concentration of 1 to 2 mg/ml using an Amicon concentration system with a PM-10 filter. Alternately, monoclonal antibody was purified from tissue culture fluid as described in Example 6.

To iodinate the purified antibody preparation, 10 to 15 μg of protein dissolved in 0.5 M sodium phosphate buffer (pH 7.25) was placed in a glass tube. One millicurie of $I^{125}$ iodine was added in 10 μl. Chloramine T was added to 25 μg from a stock of 2.5 mg/ml of 0.5 M sodium phosphate buffer (pH 7.25) to begin the iodination. After 20 seconds, 40 micrograms of sodium bisulfite was added to end the reaction. Three hundred microliters of NaI at 10 milligrams/ml were added to the reaction tube. The entire reaction volume was added to the top of a 14 ml Sephadex G100 column (1.3×15 cm; width×height). The material was chromatographed over the Sephadex column using PBS with 0.02% sodium azide and the fractions containing $I^{125}$ labelled proteins were collected and then diluted to 50,000 cpm/10 μl with PBS containing 1 mg/ml BSA and 0.02% sodium azide.

EXAMPLE 14

Immunization of Animals with Subunit Vaccine from VP-1

Adult Lewis rats were injected with 3 doses of isolated VP-1, obtained as described in Example 3. The first animal was injected on days 0, 73 and 89. The second was injected on days 0, 16, and 70. The first dose (day 0) was given subcutaneously with approximately 10 to 15 μg of VP-1 in a volume of 1.0 ml that included the isolated protein in 0.5 ml $H_2O$ and 0.5 ml complete Freund's adjuvant. The second dose (day 73 or 16) and the third dose (day 89 or 70) was given intraperitoneally and contained approximately 15 μg of VP-1/dose/animal in a volume of 0.5 ml $H_2O$ and 0.5 ml incomplete Freund's adjuvant.

Serum was collected (10 to 14d, 21d, 28d, and for several weeks) after the last injection of VP-1 and was tested for neutralization of HAV infectivity as described in Example 8. These sera were positive for the presence of neutralizing antibodies to HAV.

What is claimed is:

1. A hepatitis A surface antigen protein which has the sequence

| | | | | | | | | | |
|---|---|---|---|---|---|---|---|---|---|
| Val | Gly | Asp | Asp | Ser | Gly | Gly | Phe | Ser | Thr Thr |
| I | | | | | | | | | |
| 1918 | | | | | | | | | 1945 |
| Val | Ser | Thr | Glu | Gln | Asn | Val | Pro | Asp | Pro |
| | | | | | | | 1972 | | |
| Gln | Val | Gly | Ile | Thr | Thr | MET II | Lys | Asp | Leu |
| | | | | | | 1999 | | | |
| Lys | Gly | Lys | Ala | Asn | Arg | Gly | Lys | MET III | Asp |
| | | | | | 2026 | | | | |
| Val | Ser | Gly | Val | Gln | Ala | Pro | Val | Gly | Ala |
| | | | | 2053 | | | | | |
| Ile | Thr | Thr | Ile | Glu | Asp | Pro | Ala | Leu | Ala |
| | | | 2080 | | | | | | |
| Lys | Lys | Val | Pro | Glu | Thr | Phe | Pro | Glu | Leu |
| | | 2107 | | | | | | | |
| Lys | Pro | Gly | Glu | Ser | Arg | His | Thr | Ser | Asp |
| | 2134 | | | | | | | | |
| His | MET | Ser | Ile | Tyr | Lys | Phe | MET IV | Gly | Arp |
| 2161 | | | | | | | | | |
| Ser | His | Phe | Leu | Cys | Thr | Phe | Thr | Phe | Asn |
| 2188 | | | | | | | | | 2215 |
| Ser | Asn | Asn | Lys | Glu | Tyr | Thr | Phe | Pro | Ile |
| | | | | | | | 2242 | | |
| Thr | Leu | Ser | Ser | Thr | Ser | Asn | Pro | Pro | His |
| | | | | | | 2269 | | | |
| Gly | Leu | Pro | Ser | Thr | Leu | Arg | Trp | Phe | Phe |
| | | | | | 2296 | | | | |
| Asn | Leu | Phe | Gln | Leu | Tyr | Arg | Gly | Pro | Leu |
| | | | | 2323 | | | | | |
| Asp | Leu | Thr | Ile | Ile | Ile | Thr | Gly | Ala | Thr |
| | | | 2350 | | | | | | |
| Asp | Val | Asp | Gly | MET V | Ala | Trp | Phe | Thr | Pro |
| | | 2377 | | | | | | | |
| Val | Gly | Leu | Ala | Val | Asp | Thr | Pro | Trp | Val |
| | 2404 | | | | | | | | |
| Glu | Lys | Glu | Ser | Ala | Leu | Ser | Ile | Asp | Tyr |
| 2431 | | | | | | | | | |
| Lys | Thr | Ala | Leu | Gly | Ala | Val | Arg | Phe | Asn |
| 2458 | | | | | | | | | 2485 |
| Thr | Arg | Arg | Thr | Gly | Asn | Ile | Gln | Ile | Arg |
| 2512 | | | | | | | | | |
| Leu | Pro | Trp | Tyr | Ser | Tyr | Leu | Tyr | Ala | Val |
| | | | | | | | 2539 | | |
| Ser | Gly | Ala | Leu | Asp | Gly | Leu | Gly | Asp | Lys |
| | | | | | | 2566 | | | |
| Thr | Asp | Ser | Thr | Phe | Gly | Leu | Val | Ser | Ile |
| | | | | | 2593 | | | | |
| Gln | Ile | Ala | Asn | Tyr | Asn | His | Ser | Asp | Glu |
| | | | | 2620 | | | | | |
| Tyr | Leu | Ser | Phe | Ser | Cys | Tyr | Leu | Ser | Val |
| | | | 2647 | | | | | | |
| Thr | A | Gln | Ser | Glu | Phe | Tyr | Phe | Pro | Arg |
| | | 2674 | | | | | | | |
| Ala | Pro | Leu | Asn | Ser | Asn | Ala | MET | Leu | Ser |
| | 2701 | | | | | | | | |
| Thr | Glu | Ser | MET | MET | Ser | Arg | Ile | Ala | Ala |
| 2728 | | | | | | | | | 2755 |
| Gly | Asp | Leu | Glu | Ser | Ser | Val | Asp | Asp | Pro |
| | | | | | | | | 2782 | |
| Arg | Ser | Glu | Glu | Asp | Arg | Arg | Phe | Glu | Ser |
| | | | | | | | 2803 | | |
| His | Ile | Glu | Cys | Arg | Lys | Pro | Tyr | Lys | Glu |
| | | | | | | 2836 | | | |
| Leu | Arg | Leu | Glu | Val | Gly | Lys | Gln | Arg | Leu |
| | | | | | 2863 | | | | |
| Lys | Tyr | Ala | Gln | Glu | Glu | Leu | Ser | Asn | Glu |
| | | | | 2890 | | | | | |
| Val | Leu | Pro | Pro | Pro | Arg | Lys | MET | Lys | Gly |
| | | | 2917 | | | | | | |
| Leu | Phe | Ser | Gln | Ala | Lys | Ile | Ser | Leu | Phe |
| | | 2944 | | | | | | | |
| Tyr | Thr | Glu | Glu | His | Glu | Ile | MET | Lys | Phe |
| X | 2971 Trp | Arg | Gly | Val | | | | | |
| 2998 | | | | | | | | | | wherein X is unknown and A is either Gln or Glu.

2. A method for isolating the surface protein of claim 1 comprising:
(a) solubilizing intact hepatitis A virus in a solution containing an anionic surfactant and a reducing agent;
(b) separating by chromatographic means the viral proteins; and
(c) selecting the viral protein having a molecular weight of about 33,000 daltons.

3. A method according to claim 2 wherein the anionic surfactant is sodium dodecyl sulfate.

4. A method according to claim 2 wherein the reducing agent is 2-mercaptoethanol.

5. A method according to claim 2 wherein separating of the viral proteins is effected by gel electrophoresis.

6. A method according to claim 2 wherein the separating is effected by column chromatography.

* * * * *